United States Patent [19]

Bettinger

[11] Patent Number: 5,427,585
[45] Date of Patent: Jun. 27, 1995

[54] ON-DEMAND IONTOPHORETIC SYSTEM

[76] Inventor: David S. Bettinger, 8030 Coventry, Grosse Ile, Mich. 48138

[21] Appl. No.: 38,285

[22] Filed: Mar. 29, 1993

[51] Int. Cl.$^6$ .............................................. A61N 1/30
[52] U.S. Cl. ...................................... 604/20; 607/151
[58] Field of Search .................. 604/20; 607/149, 151, 607/152

[56] References Cited

U.S. PATENT DOCUMENTS

| | | | |
|---|---|---|---|
| 4,141,359 | 2/1979 | Jacobson et al. | 604/20 |
| 4,166,457 | 9/1979 | Jacobsen et al. | 604/20 |
| 4,702,732 | 10/1987 | Powers et al. | 604/20 |
| 4,722,726 | 2/1988 | Sanderson et al. | 604/20 |
| 4,808,152 | 2/1989 | Sibalis | 604/20 |
| 4,814,168 | 3/1989 | Sablotsky et al. | 424/78 |
| 4,842,577 | 6/1989 | Konno et al. | 604/20 |
| 4,917,676 | 4/1990 | Helber et al. | 424/449 |
| 4,917,688 | 4/1990 | Nelson et al. | 604/306 |
| 4,921,475 | 5/1990 | Sibalis | 604/20 |
| 4,942,883 | 7/1990 | Newman | 604/20 |
| 4,950,229 | 8/1990 | Sage, Jr. | 604/20 |
| 5,053,001 | 10/1991 | Reller et al. | 604/20 |
| 5,057,072 | 10/1991 | Phipps | 604/20 |
| 5,087,241 | 2/1992 | Mathiesen et al. | 604/20 |
| 5,125,894 | 6/1992 | Phipps et al. | 604/20 |
| 5,135,480 | 8/1992 | Bannon et al. | 604/20 |
| 5,188,260 | 2/1993 | Bettingher | 222/95 |
| 5,213,568 | 5/1993 | Lattin et al. | 604/20 |
| 5,234,404 | 8/1993 | Tuttle et al. | 604/20 |

OTHER PUBLICATIONS

Berner & Dinh, Fundamental Concepts in Controlled Release, pp. 2–4, "Treatise on Controlled Drug Delivery", Edited by Agis Kydonieus, Marcel Dekker, Inc. 1992.

Robert D. Lowry, "Packaging Monograph No. 1", 1963, p. 8, Packaging Institute.

J. Hadgraft & R. H. Guy, "Physicochemical Models for Percutaneous Absorption", 0097–6156/87/0348–0084 ACS, also published by Chapter 6 of Controlled-Release Technology, pp. 84–97, 1987.

Y. W. Chien & C. Lee, "Transdermal Drug Delivery System with Enhanced Skin Permeability", 0097–6156/87/0348–0281 ACS, also published as Chapter 21 of Controlled-Release Technology, pp. 281–300, 1987.

C. B. Rosdahl, RN, "Textbook of Basic Nursing", Lippincott, p. 320, 1989.

Nozawa I. Suzuki Y. Sato S. Sugibayashi K. Morimoto Y. "Preparation of thermo-responsive membranes. II." Journal of Biomedical Materials Research. [JC:hjj] 25(5):577–88, 1991 May.

Sasaki H. Kojima M. Nakamura J. Shibasaki J. "Enhancing effect of combining two pyrrolidone vehicles on transdermal drug delivery." Journal of Pharmacy & Pharmacology. [JC:jnr] 42(3):196–9, 1990 Mar.

*Primary Examiner*—C. Fred Rosenbaum
*Assistant Examiner*—Michael Rafa

[57] ABSTRACT

A transdermal medication system wherein said medication is selectively dispensed on-demand from multiple reservoirs within a disposable patch so as to vary the drug choice and the drug concentration, and thereby the regimen and release rate. In a preferred embodiment electric resistance heating activates multiple heat-shrink polymer reservoirs into an absorbent layer for transdermal passage. An embodiment of the invention dispenses a heated moisturizing fluid to facilitate transdermal transfer. In another embodiment, depletion indication is provided.

1 Claim, 1 Drawing Sheet

ON-DEMAND IONTOPHORETIC SYSTEM

Statement as to rights to inventions made under Federally-sponsored research and development.

No Federally-sponsored work was associated with this invention.

Cross-References to Related Applications. 07/709,219 Bettinger Art Unit 3108 DEROSA U.S. Pat. No. 5,188,260 Feb. 23, 1993

BACKGROUND OF THE INVENTION

1. Field of Invention

This invention generally relates to a patch for dispensing parenteral fluid medication through the skin and more particularly to a patch with one or more internal reservoirs which after adhesion to the skin is inert until medication is required. In general, patches have found usage for the ambulatory patient requiring an extended regimen such as for a chronic condition or for birth control. About half of all ethical pharmaceuticals are consumed for a chronic condition.

Berner & Dinh point out that many chronic conditions such as hormone deficiency would benefit from a regimen which was moderated to daily and weekly biorhythms. Chronic attacks of pain, diabetic imbalance, or panic may require intermittent medication administered to match severity and duration. Such attacks may also require involuntary administration. Attacks such as cardiovascular may require different drugs in different sequences depending upon severity.

Non-medical situations may require multiple doses on-demand during the operational life of a transdermal patch. An example of this would be a commercial pilot who may require a stimulant at intervals during a long flight to remain alert, based on automatic physiological sensing.

2. Description of the Prior Art

Prior art of on-demand transdermal therapeutic systems includes thermo-responsive membranes, user activated, and iontophoretic systems. Nozawa et al describes a liquid-crystal transdermal membrane which automatically dispenses medication when fever temperatures are reached. User activated systems such as Helber et al in U.S. Pat. No. 4,702,732 continuously medicate after manual activation. Iontophoretic systems such as Reller et al, U.S. Pat. No. 5,053,001, are only fully active when the power is turned on, but some drug exposure begins when the patch is applied.

Prior art on multi-drug systems include systems where a multi-drug mixture is packaged within the reservoir, or where the adhesive contains a medication different in composition from that in the reservoir. Hadgraft and Guy describe the former multi-drug mixture which may include a skin penetration enhancer (SPE). Sablotsky et al, U.S. Pat. No. 4,814,168, is representative of the latter where the adhesive contains a drug. This patent also represents the prior art on SPE for transdermal patches where the SPE is integral with the adhesive mastic. Such SPE adhesives are well described in Chien and Lee.

Variation in release rate has been a goal of prior art. U.S. Pat. No. 4,141,359 controls iontophoretic current and thus drug flow. Nelson et al in U.S. Pat. No. 4,917,688 varies the release rate by varying the external active exposed patch area prior to application. The difficulties of internal control of release rate prompted Helber et al in their U.S. Pat. No. 4,911,707 transdermal system patent to state in line 35 that "only a single release rate results per system." Within limits, drug concentration has an effect on skin absorption rate. None of these systems feature medication dispensing internal to the patch to allow variation in drug concentration.

Selective dispensing from multiple reservoirs has not been a goal of prior art. U.S. Pat. Nos. 4,921,475 and 5,053,001 both have multiple reservoirs for a single medication. They do not teach selective multiple drug dispensing.

Prior art on the use of colored indicators in connection with a transdermal Patch is described by Sasaki et al where phenol red was used in experiments to indicate comparative skin penetration.

Bettinger in U.S. Pat. No. 5,188,260 line 45 teaches the use of shrink-polymer dispensing for "delayed ambulatory medication." Lowry shows the shrink-polymer spectrum available.

SUMMARY OF THE INVENTION

1. Objects of the Invention

It is a general object of this invention to overcome the aforementioned drawbacks of prior art transdermal medication dispensing systems.

It is another general object of this invention to teach the on-demand dispensing of medication by dispensing internal to the patch. In order to meet the on-demand criteria any fluid flow within the patch must be assisted discharge. Patch use characteristics eliminate mechanical impellers. Only shrink dispensing and vapor assist meet the criteria.

It is another object of this invention to teach controlled release of medication by shrink polymer dispensers internal to the patch. It is a further object of this invention to provide an inexpensive dispenser internal to the patch which takes up little volume of space because the package is the dispenser. It is another object of this invention to provide a universal transdermal patch which can administer intravenous, intramuscular, or subcutaneous extended-regimen drugs including hormones, cardiovascular, stimulants, analgesics, and psychotropics in such combinations as may be required by the patient. It is still another object of this invention to provide a transdermal medication system capable of programmable multi-drug sequencing. It is yet another object of this invention to provide repeated intermittent medications. It is yet another object of this invention to provide a safe drug dispenser with safeguards for patient loss of consciousness or loss of cognitive ability. It is yet a further object of this invention to provide a physiological indicator of medication exhaustion. It is yet another object to enhance skin permeability by programmed release of an SPE.

2. Features of the Invention

In keeping with these objects and others which will become apparent hereinafter, one feature of this invention resides, briefly stated, in a transdermal medication system wherein said medication is selectively dispensed on-demand from multiple reservoirs within a disposable patch so as to vary drug choice and/or drug concentration.

One skilled in the art will understand that a variation of the on-demand transdermal medication system can be useful wherein the transfer of medication through the skin is aided by iontophoretic means.

A first embodiment of the invention concerns said patch wherein each said reservoir container is made of heat shrink polymer material, which when heated results in a reduction in the interior volume of said reservoir forcing said flowable fluid through said outlet and onto said absorbent layer.

A second embodiment concerns said patch wherein said reservoir heating element vaporizes a liquid and expels said flowable fluid through said outlet and onto said absorbent layer.

A third and independent embodiment concerns said patch wherein the absorbent layer contains an electric resistance heating element with means for connection to a power source or controller, whereby when heated with the simultaneous presence of a moisturizing liquid serves to prepare the skin under said patch for medication transfer to the patient's bloodstream.

Some doctors instruct a patient in the self administration of an ointment to first apply moist heat to hasten assimilation. Rosdahl's *Textbook of Basic Nursing* states that increased local blood flow results from moist heat. The moist heat generating embodiment of this invention will act as a SPE and also moderate iontophoresis skin damage.

A fourth embodiment concerns said heat shrink polymer container which achieves in its post-dispensing state a relaxed shape in which the opposing internal surfaces are adjacent and parallel so as to minimize any residual undispensed charge.

A fifth an independent embodiment of the invention concerns any transdermal medication patch wherein at or near the exhaustion of the medication the patch dispenses a drug which creates a perceptible or observable physiological change in the patient as an indicator for medication exhaustion and patch renewal. A variation of this embodiment concerns the medication exhaustion indicator wherein the indicator drug is methylene blue.

High demand may quickly deplete a patch's drug supply. The dispensing of methylene blue will color the urine, alerting an otherwise defenseless patient.

DESCRIPTION OF THE PREFERRED EMBODIMENTS

Figure 1:
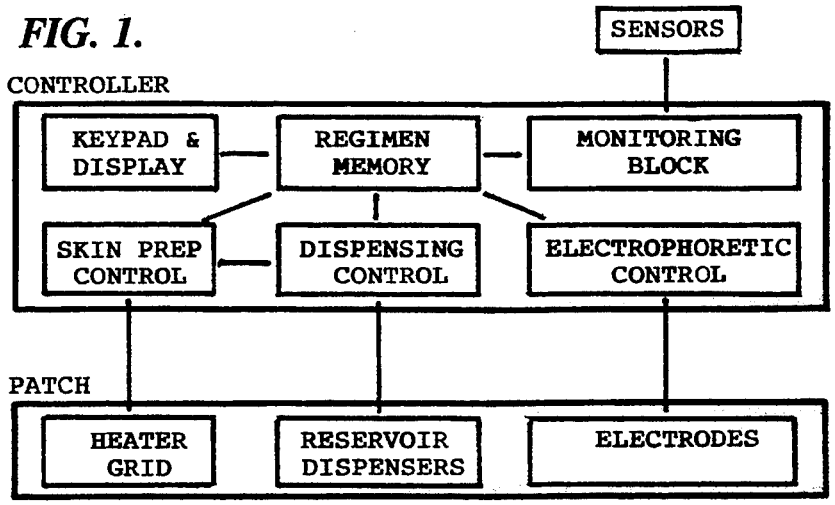
FIG. 1 is a schematic of a preferred embodiment of the transdermal medication system.

Referring now to the drawings, FIG. 1 shows the functional relationship between components of the on-demand transdermal medication system of comprising
(a) a battery power source;
(b) a microchip controller circuit;
(c) means for user control, such as a keypad;
(d) means for sensing physiological variables, such as temperature, heart rate, or skin pH;
(e) means for connecting components; and
(f) a disposable patch It will be understood by one familiar with the art that the patch may be administered to the patient's body on a site remote to system support functions.

Figure 2:
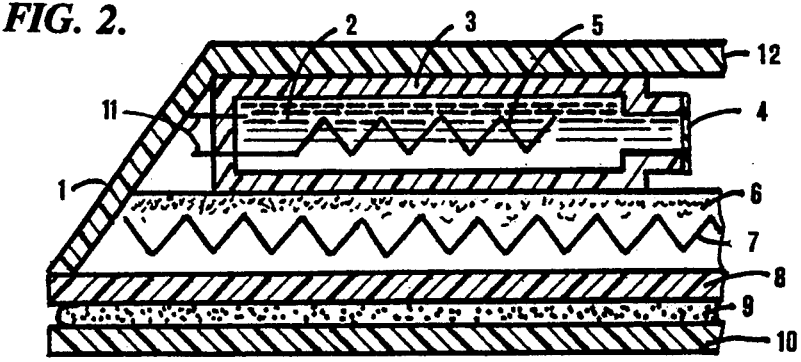
FIG. 2 is a partial section through a preferred embodiment of a transdermal patch.

FIG. 2 shows the components of said disposable patch 1 comprising a top seal layer 12; one of the multiple reservoir containers 2 each having an enclosing wall 3; said reservoirs 2 having at least one closable outlet 4 through which a flowable fluid is induced to administer a medication; and said reservoirs 2 having integral electric resistance heating elements 5 with means for connection 11 to said controller and power source and means for connecting components; and an absorbent layer 6; an electric resistance heating grid, 7; a semipermeable membrane 8; an adhesive layer for attachment to the skin 9; and a removable layer 10 to protect said membrane prior to use.

It will be understood by one skilled in the art that the shape of the reservoirs may vary to accommodate the volume within the patch, and the reservoir structure in its entirety may be embedded in the absorbent layer 5 to protect from premature dispensing due to external pressure.

Figure 3:
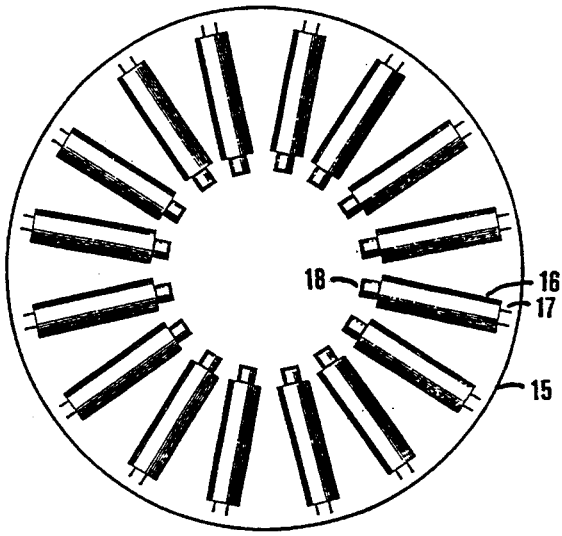
FIG. 3 is a plan view of a preferred embodiment patch with the top seal layer removed to show the multiple reservoir layer.

In FIG. 3 the multiplicity of reservoirs illustrates how various regimens may be administered from within a single transdermal patch 15. Each reservoir 16 consists of a container 16, a closable outlet 18, and electric connections 17. For example, for an acute accident victim in transit, reservoirs in the four quadrants may each respectively contain moisturizing medication, analgesic, tranquilizer, and anticonvulsant. Various drug selections and drug concentrations can be sequenced and controlled by incrementing the multiple reservoirs to meet sensor requirements.

Figure 4:
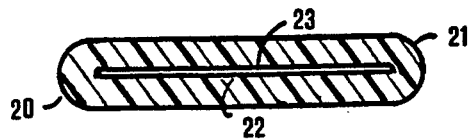
FIG. 4 is a transverse section through a heat shrink reservoir after shrinkage dispensing which reverts to a flat shape for dispensing efficiency.

FIG. 4 shows an embodiment which minimizes the reservoir volume at depletion by utilizing the shape memory of the polymer material at the two lobes 20 and 21 to bring the two opposing faces 22 and 23 of the internal surface into parallel.

What is claimed as new and desired to be protected by Letter Patent is set forth in the appended claims:

1. An iontophoretic medication patch of the type comprising a source of electrical power connected to an agent reservoir containing an agent to be transdermally delivered and an absorbent layer positioned between the agent reservoir and a skin contacting surface of the patch through which said agent is delivered, the improvement comprising wherein said absorbent layer contains an electric heating element with means for connection to a power source, and a source of moisturizing liquid within said absorbent layer, whereby when current is applied to said heating element, said patch pretreats the skin under said patch for iontophoretic delivery of agent.

* * * * *